United States Patent [19]

Stefanski et al.

[11] Patent Number: 4,622,468
[45] Date of Patent: Nov. 11, 1986

[54] FLUORESCENCE INTENSITY COMPENSATION METHOD AND DEVICE

[75] Inventors: Andrew Stefanski, Menlo Park; Alfred H. Sturtevant, Palo Alto; Michael G. Konicek, Cupertino; Peter E. Lobban, Palo Alto, all of Calif.

[73] Assignee: Sequoia-Turner Corporation, Mountain View, Calif.

[21] Appl. No.: 754,659

[22] Filed: Jul. 15, 1985

[51] Int. Cl.$^4$ ............................................ G01N 21/64
[52] U.S. Cl. ............................... 250/458.1; 250/459.1; 356/317
[58] Field of Search .............. 250/458.1, 459.1, 461.1, 250/461.2, 365; 356/317, 318

[56] References Cited

U.S. PATENT DOCUMENTS 3,854,050 12/1974 Peterson et al. .................. 250/461.2
3,918,812 11/1975 Holm ................................. 250/459.1
4,198,567 4/1980 Eneroth et al. ....................... 356/318
4,516,856 5/1985 Popelka ............................ 250/458.1

Primary Examiner—Carolyn E. Fields
Attorney, Agent, or Firm—Limbach, Limbach & Sutton

[57] ABSTRACT

Variations in the intensity of a light source and the sensitivity of a fluorescence detector photo-multiplier tube are simultaneously compensated by measuring the intensity ($I_{LS1}$) of the light source at the sample excitation frequency with a silicon detector, measuring the intensity ($I_{LS2}$) of the light source at the emission frequency with another silicon detector, measuring with the photo-multiplier detector the intensity ($I_S$) of the sample's fluorescence and the intensity ($I_{LS3}$) of the light source at the emission frequency of the sample and then calculating a value F as representative of the sample's fluorescence according to the formula:

$$F = \frac{I_S \times I_{LS2}}{I_{LS3} \times I_{LS1}}$$

7 Claims, 2 Drawing Figures

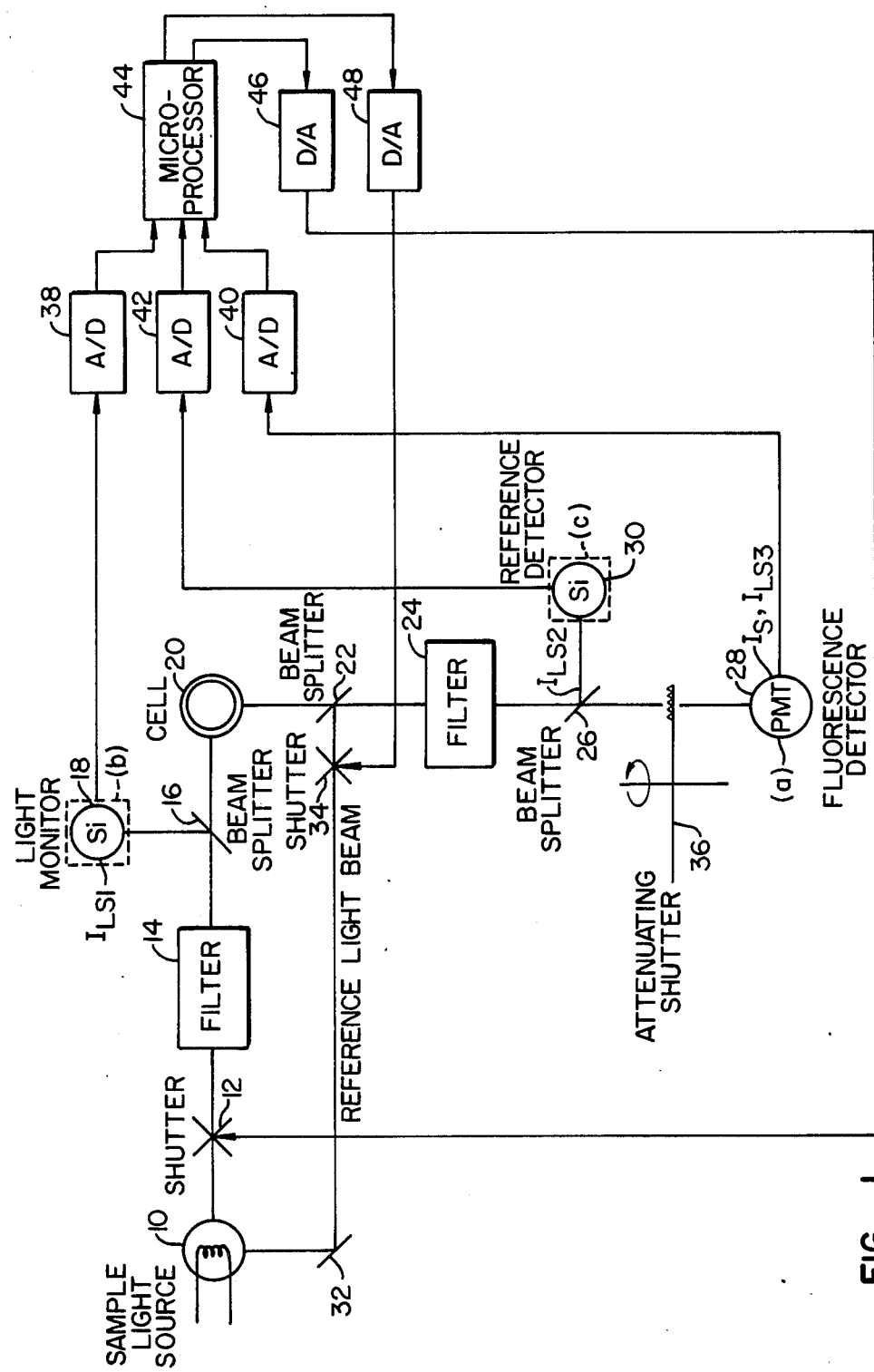
FIG._1.

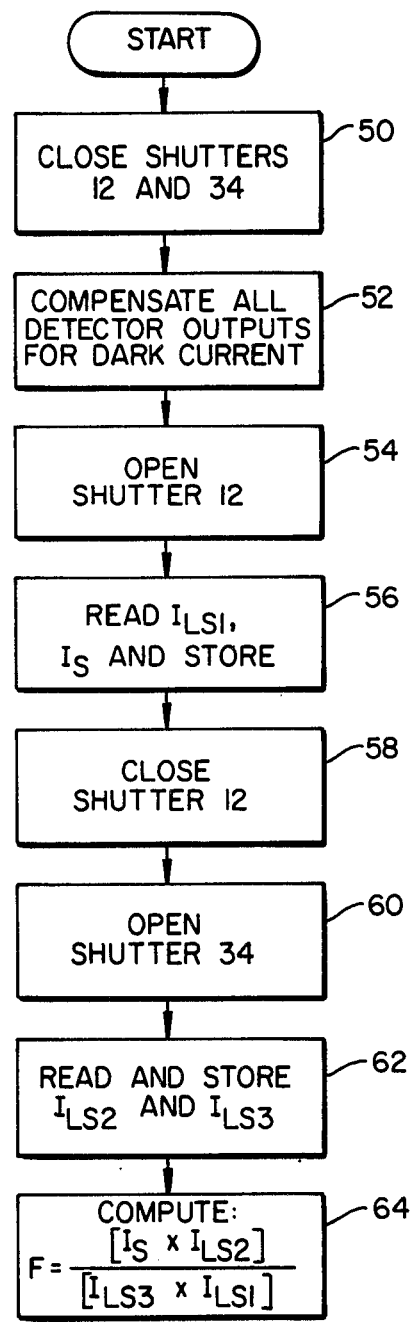
FIG._2.

FLUORESCENCE INTENSITY COMPENSATION METHOD AND DEVICE

DESCRIPTION

1. Technical Field

The invention relates to a fluorescence detection system and, more particularly, to a compensation circuit for such a system.

2. Background Art

In a fluorescence detection system, a source of light is shone on a sample and the fluorescence from the sample is then analyzed. Most existing systems provide compensation for variations in lamp intensity or compensation for changes in the fluorescent light detector sensitivity, but not for changes in both the light intensity and the photodetector sensitivity. In most cases, the photodetector is a photo-multiplier tube. Those systems which do provide compensation for either source of error use the same wavelength of light for compensating for both types of error. That is, changes in the light intensity of the source are measured at a wavelength which is the same wavelength that is used to check for variations in the sensitivity of the photo-multiplier tube. This introduces error, however, since it is the sensitivity of the photo-multiplier tube at the wavelength of the fluorescence which must be compensated.

What is needed is a system which will give extremely stable readings over a long period of both continuous and discontinuous use and over large changes in the ambient temperature. The compensation system must be reliable and relatively simple in operation.

SUMMARY OF THE INVENTION

The above and other problems of prior art fluorescence detection compensation systems are overcome by the present method and apparatus of a fluorescence detection system of the type wherein a source of light at an excitation frequency is shone on a sample to cause it to fluoresce at an emission frequency which is detected by a detector a. The improvement comprises sensing the intensity of the light source at the excitation frequency by a second detector b, sensing the intensity of the light source at the emission frequency with a third detector c, and sensing the intensity of the light source at the emission frequency with the a detector and deriving a value F which represents the fluorescence of the sample by combining the outputs of the detectors according to the formula:

$$F = \frac{I_S \times I_{LS2}}{I_{LS3} \times I_{LS1}}$$

where
- $I_S$ = Output of detector a when sensing the light fluoresced from the sample.
- $I_{LS1}$ = Output of detector b when sensing the light source intensity at the excitation frequency.
- $I_{LS2}$ = Output of detector c when sensing the light source intensity at the emission frequency.
- $I_{LS3}$ = Output of detector a when sensing the light source intensity at the emission frequency.

In the preferred embodiment of the invention, the detector a is a photo-multiplier tube and the detectors b and c are silicon detectors. A first beam splitter is interposed between the light source and the sample to deflect a portion of the light to the detector b. A second beam splitter is interposed between the sample and the detector a to deflect a portion of the light which would otherwise be received by the detector a to the detector c. A third beam splitter is interposed between the sample and the second beam splitter to allow the light source to be shone directly upon the detectors a and c during the referencing step. During this step, the sample is prevented from fluorescing by means of a first shutter which is interposed between the light source and the sample. When the sample is being illuminated, a second shutter stops light from the light source from hitting the third beam splitter.

While a reading of the intensity of the cell's fluorescence can be done manually according to the above-noted formula, in the preferred embodiment, the outputs of the separate detectors are converted to digital signals by separate analogue to digital converters and are input to a microprocessor which computes the value F. The microprocessor, through digital to analogue converters, can also control the first and second shutters to perform the compensation routine automatically.

It is therefore an object of the invention to provide simultaneous light source intensity and photodetector sensitivity compensation in a fluorescence analysis system.

It is another object of the invention to provide a compensation system which simultaneously compensates for changes in the light source intensity at the excitation frequency and changes in the sensitivity of the photodetector at the emission frequency.

The foregoing and other objectives, features and advantages of the invention will be more readily understood upon consideration of the following detailed description of certain preferred embodiments of the invention, taken in conjunction with the accompanying drawings.

BRIEF DESCRIPTION OF THE DRAWINGS

FIG. 1 is a block diagram illustrating the operation of the fluorescence detector system according to the invention; and FIG. 2 is a flow chart illustrating the operation of the computer depicted in FIG. 1.

BEST MODE FOR CARRYING OUT THE INVENTION

Referring now more particularly to FIG. 1, a light source 10 is used for illuminating a sample 20. The light source could be a quartz halogen lamp, a light emitting diode, a laser, or any other type of lamp. Interposed between the light source 10 and the sample cell 20 are a shutter 12, an excitation filter 14, and a beam splitter 16. The purpose of the filter 14 is to allow only light at the excitation frequency from the light source 10 to impinge upon the cell 20. The light source 10 could be a monochromatic light source, such as a laser or a light emitting diode, for example, in which case the filter 14 could be omitted provided the light source frequency was correctly chosen. However, a second lamp would be required to provide light at the emission frequency for the compensation signal.

The purpose of the beam splitter 16 is to divert a portion of the light from the source 10 to a silicon detector light monitor 18. The output from the detector 18 is an electronic signal $I_{LS1}$ which represents the intensity of the light source 10 at the excitation frequency. A photo-multiplier tube 28 observes the light fluoresced from the sample 20. Interposed between the photo-multiplier tube 28 and the sample cell 20 is a beam splitter 22, an emission filter 24, and a second beam splitter 26. The beam splitter 26 diverts a portion of the light passing through the filter 24 to a second silicon detector light monitor 30.

The photo-multiplier tube ("PMT") 28 is highly sensitive to light, much more so than the silicon detector 30. But the PMT is less stable over time and with changes in the ambient temperature than the silicon detector 30. By referencing the readings of the PMT 28 to the readings of the silicon detector 30, compensation can be made for changes in the sensitivity of the PMT 28.

Light from the source 10 is reflected by means of a mirror 32 to pass through a shutter 34 and to strike the beam splitter 22. The alignment of the source 10, the mirror 32, and the beam splitter 22 is such that light from the source 10 striking the beam splitter 22 will be reflected to the photo-mulitiplier tube 28 and, through the beam splitter 26, to the detector 30.

In operation, the shutter 12 or the shutter 34 can be open, but both shutters cannot be open at the same time. When the shutter 34 is closed, and the shutter 12 is open, light from the source 10 passes through the filter 14 and a portion of it will strike the cell 20 and a portion will strike the detector 18. The cell 20 will fluoresce and produce a light beam which passes through the beam splitter 22, the filter 24, and divides at the beam splitter 26 to impinge partly on the photo-multiplier tube 28 and partly on the detector 30. The photo-multiplier tube 28 converts the light intensity to an electronic signal $I_S$ which represents the intensity of the fluoresced light. The output of the detector 30 at this point is ignored.

Thereafter, the shutter 12 is closed and the shutter 34 is opened. Now, with no light hitting the cell 20, there is no fluorescence. The light from the source 10 is reflected by means of the mirror 32 and the beam splitter 22 through the filter 24 to impinge partially on the photo-multiplier tube 28 and partially on the silicon detector 30. The electronic signal produced at the output of the photo-multiplier tube 28 is $I_{LS3}$. The output of the detector 30 is an electronic signal $I_{LS2}$. In some embodiments, it is necessary to interpose an attenuator 36 between the beam splitter 26 and the photo-multiplier tube 28 to make the outputs of the detectors 28 and 30 roughly equivalent. The attenuator 36 is only interposed when the shutter 34 is open.

Fluorescence may now be calculated using the formula $$F = \frac{I_S \times I_{LS2}}{I_{LS3} \times I_{LS1}}$$

The values $I_S$, $I_{LS1}$, $I_{LS2}$, and $I_{LS3}$ are electric current magnitudes in the above described embodiments, however, they could instead be voltages.

In the preferred embodiment of this system, the detectors 18, 28 and 30 are also corrected for dark current by closing both shutters 12 and 34 simultaneously and nulling the outputs of the detectors.

While the above operation of opening and closing the shutters and taking the detector readings can be performed manually, in the preferred embodiment of the invention it is done automatically. The outputs of the detectors 18, 28, and 30 are converted from analogue waveforms to digital waveforms by separate analogue to digital converters 38, 40, and 42, respectively, which are then supplied as inputs into a microprocessor 44.

The microprocessor, in turn, by means of a stored program makes the calculation for F and also, through separate digital to analogue converters 46 and 48, controls the opening and closing of the shutters 12 and 34 to carry out the above noted sequence of steps. It should be understood that the microprocessor is part of the preferred embodiment, but is not necessary for the operation of the system.

Referring now more particularly to FIG. 2, the sequence of operations performed by the computer is illustrated in flow chart fashion. At step 50, the microprocessor 44 closes the shutters 12 and 34 by sending appropriate control signals through the digital to analogue converters 46 and 48. At step 52, it nulls the detector outputs for dark current readings. At step 54, the microprocessor 44 opens shutter 12. It next reads the currents $I_{LS1}$, $I_S$ from the detectors 18 and 28 and stores these values in memory at step 56. At step 58, the microprocessor closes shutter 12 and opens shutter 34 at step 60. It then reads and stores the currents $I_{LS2}$ and $I_{LS3}$ which are output by the detectors 30 and 28, respectively at step 62. At step 64, the microprocessor computes fluorescence (F) according to the formula using the stored values for the respective currents from the detectors.

While the shutters 12 and 34 may be electro-mechanical shutters, they can also be electro-optical shutters using birefringent crystals.

The terms and expressions which have been employed here are used as terms of description and not of limitations, and there is no intention, in the use of such terms and expressions, of excluding equivalents of the features shown and described, or portions thereof, it being recognized that various modifications are possible within the scope of the invention claimed.

We claim:

1. In a method of fluorescence detection wherein a light source of a first predetermined wavelength is shone on a sample and the intensity ($I_S$) of the fluorescence from the sample at a second predetermined wavelength is detected by a detector a, the improvement comprising the steps of sensing the intensity ($I_{LS1}$) of the light source at the first predetermined wavelength by a detector b, sensing the intensity ($I_{LS2}$) of the light source at the second predetermined wavelength with a detector c, sensing the intensity ($I_{LS3}$) of the light source at the second predetermined wavelength with the detector a, and deriving a value F representing the fluorescence of the sample by combining the detected intensities according to the formula:

$$F = \frac{I_S \times I_{LS2}}{I_{LS3} \times I_{LS1}}$$

2. A method as recited in claim 1 wherein the measurements $I_S$ and $I_{LS1}$ are made simultaneously and the measurements $I_{LS2}$ and $I_{LS3}$ are made simultaneously.

3. Apparatus for fluorescence analysis of a sample, comprising a source for shining light at an excitation frequency on the sample, a detector b for monitoring the intensity of the light shown on the sample at the excitation frequency and for producing an electronic output signal, $I_{LS1}$, corresponding thereto, a detector c for monitoring the intensity of the light source at an emission frequency, corresponding to the frequency of light emitted due to fluorescence of the sample caused by the light source, and for producing an electronic output signal, $I_{LS2}$, corresponding thereto, a detector a which produces an electronic output signal $I_S$ corresponding to the intensity of light at the emission frequency received from the sample due to fluorescence by the light source and an electronic output signal $I_{LS3}$ corresponding to the intensity of the light source at the emission frequency, and means supplied with the electronic signals $I_S$, $I_{LS1}$, $I_{LS2}$ and $I_{LS3}$ for generating an electronic signal F where:

$$F = \frac{I_S \times I_{LS2}}{I_{LS3} \times I_{LS1}}$$

4. Apparatus as recited in claim 3, further comprising a first shutter interposed between the light source and the sample, a second shutter interposed between the light source and both of the detectors a and c, and means for ensuring that the first and second shutters only open alternatively.

5. Apparatus as recited in claim 3 wherein detector a is a photo-multiplier tube.

6. Apparatus as recited in claim 5 wherein detectors b and c are silicon detectors.

7. Apparatus as recited in claim 3 wherein the means for generating F comprise computing means and means for separately inputting the detector outputs into the computing means and wherein the computing means combines the detector outputs to determine F according to said formula.

* * * * *